(12) United States Patent
Shin et al.

(10) Patent No.: US 11,839,681 B2
(45) Date of Patent: Dec. 12, 2023

(54) CHARCOAL-CONTAINING DOUBLE CAPSULE AND METHOD FOR MANUFACTURING SAME

(71) Applicant: BIOGENICS, INC., Daejeon (KR)

(72) Inventors: Chan-Jae Shin, Daejeon (KR); Tae-Sung Ko, Sejong (KR); Hyun-Gyu Shin, Daejeon (KR); Jeong-Ho Park, Daejeon (KR)

(73) Assignee: BIOGENICS, INC., Daejeon (KR)

( * ) Notice: Subject to any disclaimer, the term of this patent is extended or adjusted under 35 U.S.C. 154(b) by 100 days.

(21) Appl. No.: 15/734,294

(22) PCT Filed: Aug. 31, 2018

(86) PCT No.: PCT/KR2018/010149
§ 371 (c)(1),
(2) Date: Dec. 2, 2020

(87) PCT Pub. No.: WO2020/013380
PCT Pub. Date: Jan. 16, 2020

(65) Prior Publication Data
US 2021/0220253 A1    Jul. 22, 2021

(30) Foreign Application Priority Data

Jul. 13, 2018  (KR) .................. 10-2018-0081457

(51) Int. Cl.

| | | |
|---|---|---|
| *A61Q 11/00* | (2006.01) |
| *A61Q 19/00* | (2006.01) |
| *A61K 9/24* | (2006.01) |
| *A61K 8/11* | (2006.01) |
| *A61K 9/50* | (2006.01) |
| *A61K 9/48* | (2006.01) |
| *A61K 8/97* | (2017.01) |
| *A61K 8/25* | (2006.01) |
| *A61K 8/29* | (2006.01) |
| *A61K 8/73* | (2006.01) |

(52) U.S. Cl.
CPC .................. *A61K 8/97* (2013.01); *A61K 8/25* (2013.01); *A61K 8/29* (2013.01); *A61K 8/732* (2013.01); *A61Q 11/00* (2013.01); *A61Q 19/00* (2013.01); *A61K 2800/41* (2013.01); *A61K 2800/56* (2013.01)

(58) Field of Classification Search
CPC ...... A61K 8/11; A61K 2800/412; A61K 9/50; A61K 2800/56; A61K 9/00; A61K 47/38; A61K 8/73; A61K 9/4816; A61K 49/0091; A61K 9/4891; A61K 9/48; A61Q 11/00; A61Q 19/00
See application file for complete search history.

(56) References Cited

U.S. PATENT DOCUMENTS

| | | | |
|---|---|---|---|
| 5,714,445 A | 2/1998 | Trinh et al. | |
| 6,355,260 B1 * | 3/2002 | Tanaka .................. | B82Y 30/00 424/490 |
| 2003/0215417 A1 * | 11/2003 | Uchiyama ............ | C11D 3/2093 424/76.2 |
| 2006/0051425 A1 * | 3/2006 | Kvitnitsky .............. | A61P 43/00 424/769 |
| 2009/0035557 A1 * | 2/2009 | Hartmann ............. | F28D 20/023 428/323 |
| 2011/0150954 A1 * | 6/2011 | Lapidot .................... | A61Q 1/02 426/89 |
| 2014/0106032 A1 * | 4/2014 | Dardelle .............. | A61K 9/5089 426/89 |
| 2017/0071865 A1 * | 3/2017 | Goldstein ............ | A61K 9/5078 |
| 2018/0263869 A1 * | 9/2018 | Halpern Chirch ..... | A61Q 19/10 |

FOREIGN PATENT DOCUMENTS

| | | | |
|---|---|---|---|
| CN | 103417390 A | 12/2013 | |
| JP | 61225115 A * | 10/1986 | |
| JP | 2002348222 A * | 12/2002 | |
| KR | 1020010011879 A | 2/2001 | |
| KR | 1020040052929 A | 6/2004 | |
| KR | 1020050025218 A | 3/2005 | |
| KR | 1020080083080 A | 9/2008 | |
| KR | 1020100112663 A | 11/2011 | |
| KR | 1020130067004 A | 6/2013 | |
| WO | WO-2011060945 A2 * | 5/2011 | ........... A61K 31/202 |

* cited by examiner

*Primary Examiner* — Tracy Liu
(74) *Attorney, Agent, or Firm* — THE WEBB LAW FIRM

(57) ABSTRACT

The present invention includes: 1) dissolving a first binder in a first solvent; 2) dissolving a dispersing agent in a solution in which the first binder is dissolved; 3) adding charcoal powder to the solution obtained in 2) and performing homogenous mixing to produce a dispersion in which the charcoal powder is bound to the first binder; 4) spray drying the dispersion obtained in 3) to produce a primary capsule from which the first solvent is removed; 5) dissolving a second binder and a softening agent in a second solvent; 6) homogeneously mixing a coloring agent and the dispersing agent with a solution in which the second binder and the softening agent are dissolved; 7) mixing the primary capsule with the solution obtained in 6) to produce a double capsule dispersion in which the primary capsule is bound to the second binder; and 8) spray-drying the double capsule dispersion to product a double capsule from which the second solvent is removed.

12 Claims, 3 Drawing Sheets

[FIG. 1]
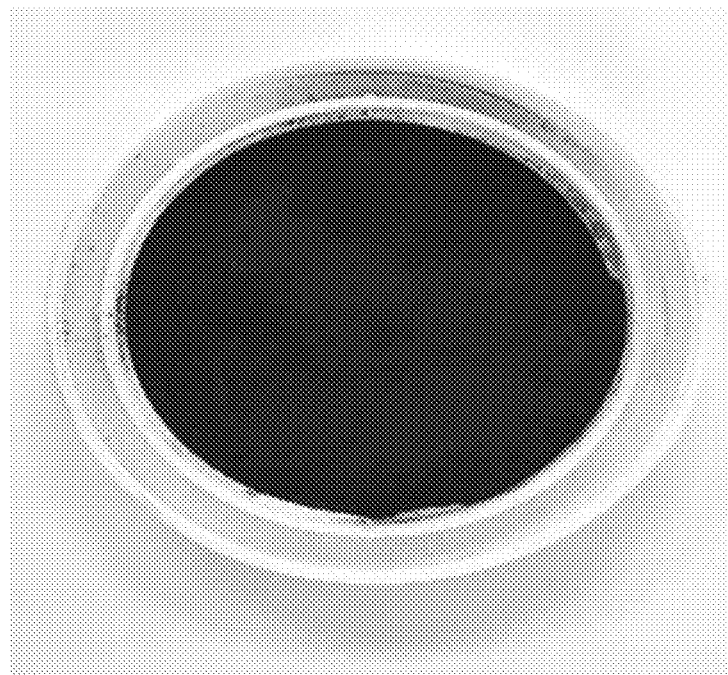
Coconut charcoal powder
[FIG. 2]
Primary capsule powder

[FIG. 3]
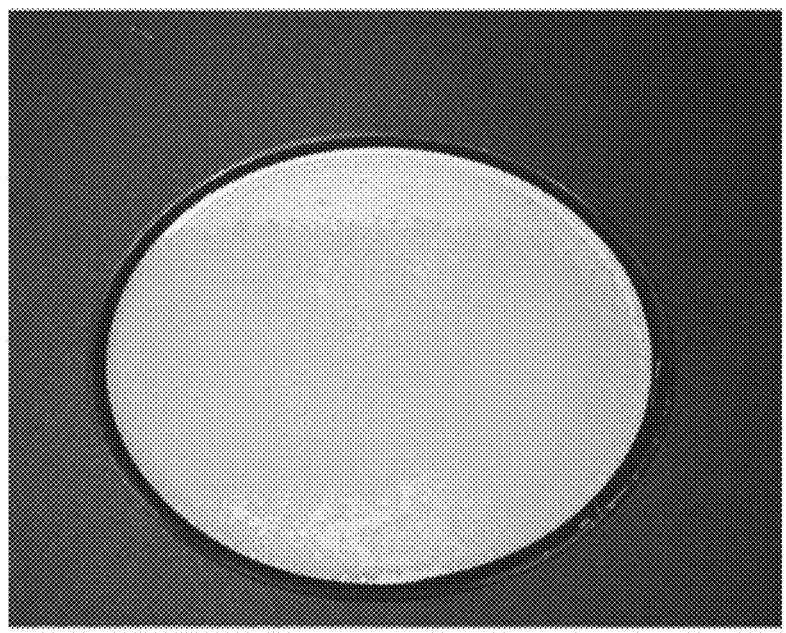
Double capsule powder
[FIG. 4]
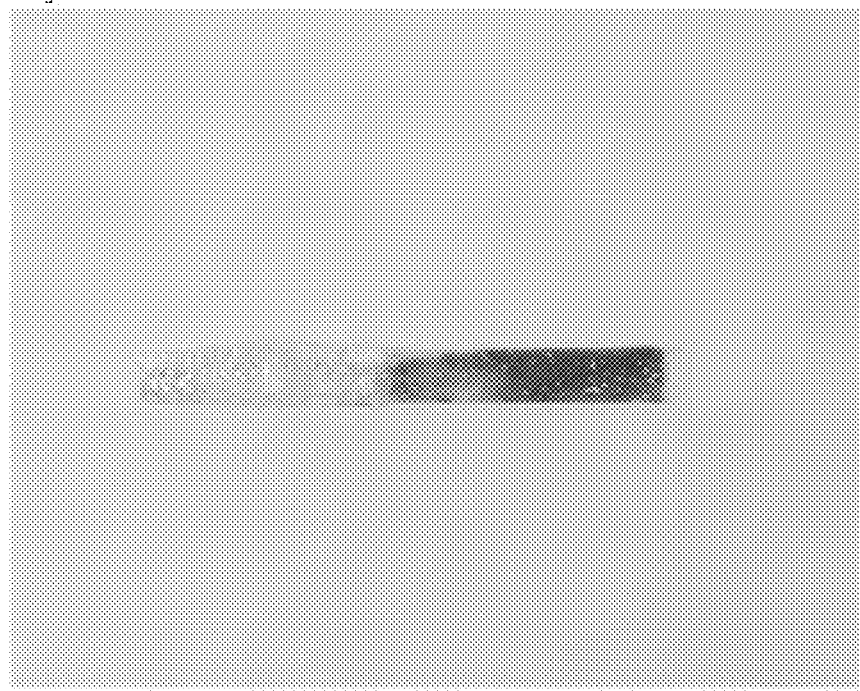
Toothpaste composition application (capsule breakage)

[FIG. 5]
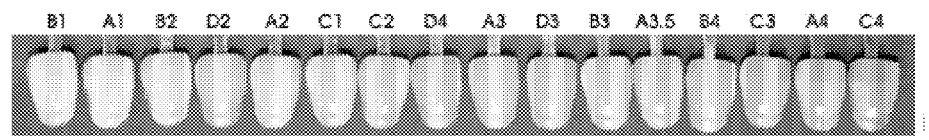

CHARCOAL-CONTAINING DOUBLE CAPSULE AND METHOD FOR MANUFACTURING SAME

CROSS-REFERENCE TO RELATED APPLICATIONS

This application is the United States national phase of International Application No. PCT/KR2018/010149 filed Aug. 31, 2018, and claims priority to Korean Patent Application No. 10-2018-0081457 filed Jul. 13, 2018, the disclosures of which are hereby incorporated by reference in their entirety.

BACKGROUND OF THE INVENTION

Field of the Invention

The present invention relates to a charcoal-containing double capsule in which charcoal powder is doubly encapsulated, so that a bright color image may be maintained even when mixed in toothpaste, cosmetics, and the like and the original color is revealed only when the capsule is broken at the time of use, and a method for manufacturing the same.

Description of Related Art

In general, charcoal includes numerous pores due to the characteristic produced during the manufacturing process. Charcoal has a surface area of 500-1400 $m^2$ per 1 g, and thus, may be a material having a significantly large specific surface area relative to the size visible to the naked eye. Further, as another characteristic, charcoal has a negatively charged characteristic, which allows it to attract positively charged molecules to itself from various chemical materials.

For example, when charcoal is applied to toothpaste, dental plaque present in teeth and gums may be adsorbed and bound to a charcoal component to manage oral hygiene, and when charcoal is applied to a cleansing foam, sebum in the pores may be adsorbed and bound to the charcoal component to help clean skin care.

There is an example in which charcoal powder used as a conventional cosmetic has been used as one of the components in a cosmetic soap, but which is used in the composition of the cosmetic soap for simply strengthening a detergent function with the adsorptive power and the like of the charcoal powder itself, and in this case, black coloring which is one other characteristics of charcoal in addition to strengthening of adsorptive power or moisturizing function becomes a factor of inhibiting improvement of a skin care effect.

When charcoal is used in toothpaste and cosmetics, conventionally, charcoal powder is used in the form of being simply mixed to represent the product color black, which shows a visually unsanitary image, and thus, may decrease consumers' purchasing needs and lower a commercial value.

SUMMARY OF THE INVENTION

An object of the present invention is to provide a charcoal-containing double capsule which may overcome a conventional disadvantage of not giving a hygienically clean feeling when visually seen to maintain a product color in a bright tone and reveal the original charcoal color only when the capsule is broken at the time of use, by doubly encapsulating charcoal powder, and a method for manufacturing the same.

Another object of the present invention is to provide a charcoal-containing double capsule in which charcoal may be doubly encapsulated to adjust capsule breaking depending on friction strength, and a method for manufacturing the same.

Technical Solution

In one general aspect, a charcoal-containing double capsule includes: a) a primary capsule in which charcoal powder is bound to a first binder, wherein b) in the double capsule, the primary capsule and a coloring agent are bound to a second binder.

Preferably, the primary capsule may have an average diameter of 10 μm to 200 μm and the double capsule may have an average diameter of 150 μm to 300 μm.

In another general aspect, a method for manufacturing a charcoal-containing double capsule includes: 1) dissolving a first binder in a first solvent; 2) dissolving a dispersing agent in a solution in which the first binder is dissolved; 3) adding charcoal powder to the solution obtained in 2) and performing homogenous mixing to produce a dispersion in which the charcoal powder is bound to the first binder; 4) spray-drying the dispersion obtained in 3) to produce a primary capsule from which the first solvent is removed; 5) dissolving a second binder and a softening agent in a second solvent; 6) homogeneously mixing a coloring agent and the dispersing agent with a solution in which the second binder and the softening agent are dissolved; 7) mixing the primary capsule with the solution obtained in 6) to produce a double capsule dispersion in which the primary capsule is bound to the second binder; and 8) spray-drying the double capsule dispersion to produce a double capsule powder from which the second solvent is removed.

Preferably, the first binder may be a modified starch selected from acetylated distarch adipate, acetylated distarch phosphate, starch sodium octenyl succinate, distarch phosphate, monostarch phosphate, phosphated distarch phosphate, starch acetate, and hydroxypropyl distarch phosphate; or a natural starch selected from the group consisting of a wheat starch, a rice starch, a potato starch, a corn starch, and the like.

Preferably, the charcoal powder may be one selected from a Northern bamboo charcoal, a bamboo charcoal, an oak charcoal, and a coconut charcoal as an activated charcoal.

Preferably, the dispersing agent may be any one selected from the group consisting of sorbitan trioleate, sorbitan stearate, sorbitan palmitate, sorbitan laurate, polyglyceryl-2 oleyl ether, polyglyceryl-6 pentaoleate, polyoxyethylene glyceryl monostearate, polyglyceryl-10 stearate, and the like.

Preferably, the second solvent may be any one or two or more selected from the group consisting of ethanol, glycerin, 1,2-propanediol, 1,3-propanediol, 1,3-butanediol, 1,4-butanediol, 1,6-hexanediol, 1,8-octanediol, and the like.

Preferably, the second binder may be one or two or more selected from natural substance-derived polymers selected from ethyl cellulose, methyl cellulose, and hydroxylpropyl cellulose, casein, shellac, and the like; and ammonium methacrylate-based polymers, methacrylic acid-based polymers, 2-dimethylaminoethyl methacrylate-based polymers, chlorotrimethylammoniumethyl methacrylate-based polymers, and copolymers thereof.

Preferably, as the softening agent, higher fatty acids such as a lauric acid, a stearic acid, and a palmitic acid may be used.

Advantageous Effects

Since the charcoal-containing double capsule according to the present invention is obtained by doubly encapsulating charcoal powder, it may maintain a product color in a bright tone even when mixed in cosmetics or toothpaste formulation, and may reveal an original charcoal color only when the capsule is broken at a constant pressure at the time of use.

In addition, since the charcoal powder is doubly encapsulated, an activated charcoal which may be deteriorated by moisture or oxygen over time due to adsorption, surface oxidation, and reduction reactivity as the characteristics of the activated charcoal, may be protected stably for a long time.

In addition, a disadvantage of the conventional cosmetics and toothpaste formulation containing charcoal which may show a visually unsanitary image is overcome, and thus, though charcoal is contained, the color may be maintained in a bright tone.

BRIEF DESCRIPTION OF THE DRAWINGS

FIG. 1 is a photograph of coconut charcoal powder used in the Example of the present invention.

FIG. 2 is a photograph of primary capsule powder prepared in the Example of the present invention.

FIG. 3 is a photograph of double capsule powder prepared in the Example of the present invention.

FIG. 4 is a photograph confirming breakability of double capsule toothpaste manufactured in the Example of the present invention.

FIG. 5 is a photograph of a 16-step tooth comparison chart.

DESCRIPTION OF THE INVENTION

Hereinafter, embodiments of the present invention will be described with reference to the accompanying drawings.

The charcoal-containing double capsule according to the present invention includes: a) a primary capsule in which charcoal is bound in a first binder, wherein b) in the double capsule, the primary capsule and a coloring agent are bound in a second binder.

First, a process of manufacturing the primary capsule includes: 1) dissolving a first binder in a first solvent; 2) dissolving a dispersing agent in a solvent in which the first binder is dissolved; 3) adding charcoal powder to the solution obtained in 2) and performing homogeneous mixing to produce a dispersion in which the charcoal powder is bound to the first binder; and 4) spray-drying the dispersion obtained in 3) to produce primary capsule powder from which the first solvent is removed.

The first solvent is preferably distilled water in which the first binder and the dispersing agent may be dissolved.

The first binder is bound to or forms an interconnection network with the discontinuously dispersed charcoal powder and adjusts viscosity. The first binder is used at 4-10 wt % with respect to a primary capsule mixture. When the first binder is used at less than 4 wt %, it is not bound to the charcoal powder well so that the primary capsule is not formed well, and when the first binder is used at more than 10 wt %, capsule strength is too high so that the capsule is not broken well. Thereafter, when used in a double capsule process, in the case in which primary capsule strength is high, double capsule strength is affected, and thus, an appropriate content should be selected. However, when a primary capsule having excessively low strength is used, stability is deteriorated so that the capsule may be broken, and thus, attention should be paid thereto. As the first binder, any one or two or more selected from modified starches selected from the group consisting of acetylated distarch adipate, acetylated distarch phosphate, starch sodium octenyl succinate, distarch phosphate, monostarch phosphate, phosphated distarch phosphate, starch acetate, hydroxypropyl distarch phosphate, and the like; and natural starches selected from the group consisting of a wheat starch, a rice starch, a potato starch, a corn starch, and the like, may be used. In particular, the natural starch was confirmed to have excellent binding strength with coconut charcoal, and also to significantly decrease disadvantages such as a bleeding phenomenon at the time of preparation of a composition in a bulk phase, and to suppress a leaching phenomenon of a microcapsule (strength degradation of a microcapsule) due to immediate breakage or rapid wetting or dissolution by water, alcohols, or the like at the time of coating.

The activated charcoal is used for giving teeth a whitening effect by being bound to impurities or bacteria in the mouth and discharged. Charcoal has a particle size of 1-10 μm and is contained at 70-94 wt % in the primary capsule mixture. Here, when the content is less than 70 wt %, a charcoal-containing capsule may not be manufactured, and when a too small amount of charcoal is used in application in a toothpaste composition, charcoal efficacy may not be expected. When the content is more than 94 wt %, it is difficult to control capsule particles to have a certain shape. As charcoal, a Northern bamboo charcoal, a bamboo charcoal, an oak charcoal, a coconut charcoal, and the like are used, but it is preferred to use charcoal in the form of an activated charcoal subjected to a specific heat treatment process. In particular, it is most preferred to use a coconut charcoal which is a kind of activated charcoal, and when charcoal is used in the form of an activated charcoal, porosity may be increased as compared with common charcoal to increase adsorption performance of plaque.

The dispersing agent disperses the charcoal powder so that the charcoal powder is uniformly positioned in the first solvent. As the dispersing agent, any one selected from the group consisting of sorbitan trioleate, sorbitan stearate, sorbitan palmitate, sorbitan laurate, polyglyceryl-2 oleyl ether, polyglyceryl-6 pentaoleate, polyoxyethylene glyceryl monostearate, polyglyceryl-10 stearate, and the like are used, which are non-ionic and have both water solubility and oil solubility to improve solubilization in oil and water. The dispersing agent is used at 2-6 wt % with respect to the primary capsule mixture. Here, when used at less than 2 wt %, the charcoal powder is not evenly dispersed in the first solvent, and when used at more than 6 wt %, a binding property of the binder is decreased to weaken the strength of the primary capsule, causing a concern of damage during a manufacturing process.

The primary capsule powder is produced by spray-drying the primary capsule dispersion to remove the first solvent, which is then subjected to sieve classification to selectively produce powder having an average diameter of 10 μm to 200 μm, preferably 15 μm to 150 μm, and more preferably 20 μm to 130 μm.

Meanwhile, a process of manufacturing the double capsule includes: 5) dissolving a second binder and a softening agent in a second solvent; 6) mixing a coloring agent and the dispersing agent in a solution in which the second binder and the softening agent are dissolved; thereafter, 7) mixing the primary capsule powder with the solution obtained in 6) to produce a double capsule dispersion in which the primary capsule is bound to the second binder; and 8) spray-drying the double capsule dispersion to produce double capsule powder.

The second solvent is preferably ethanol which may dissolve the second binder and the softening agent, and evenly disperses the primary capsule, the coloring agent, and the dispersing agent. The second solvent preferably has a lower alkyl group having 1 to 7 carbon atoms. For example, the second solvent may be any one or in a mixed form of two or more selected from ethanol, glycerin, 1,2-propanediol, 1,3-propanediol, 1,3-butanediol, 1,4-butanediol, 1,6-hexanediol, 1,8-octanediol, and the like.

The second binder is used for wrapping the primary capsule to prevent the primary capsule from being dispersed. The second binder is used at 1-6 wt % with respect to a double capsule mixture. When the second binder is used at less than 1 wt %, capsule strength is too low so that the capsule may be easily broken after the manufacturing process, and when used at more than 10 wt %, the strength is too high when forming the capsule, so that the capsule is not easily broken even when external force is applied and the effect of a whitening agent is not rapidly obtained. As the second binder, any one or two or more selected from natural substance-derived polymers selected from ethyl cellulose, methyl cellulose, hydroxylpropyl cellulose, casein, shellac, and the like; and ammonium methacrylate-based polymers, methacrylic acid-based polymers, 2-dimethylaminoethyl methacrylate-based polymers, chlorotrimethylammonium-ethyl methacrylate-based polymers, and copolymers thereof, are used.

Here, as the second binder, it is preferred to use a binder having a different solubility from the first binder. In order that a size of each microparticle is uniformly controlled to homogeneously wrap each particle when spray-drying the double capsule, viscosity of the dispersion plays an important role, and it is preferred to use cellulose derivatives which is easy to control viscosity.

The primary capsule is used at 26-40 wt % with respect to the double capsule mixture. When the primary capsule is used at less than 26 wt %, a capsule containing charcoal at a certain content may not be manufactured, and when used at more than 40 wt %, the primary capsule is not uniformly coated.

The softening agent serves to relieve excessive hardening of capsule strength due to the binder. As the softening agent, it is preferred to use a higher fatty acid of any one selected from the group consisting of a lauric acid, a stearic acid, a palmitic acid, and the like. The softening agent is used at 3-5 wt % with respect to the double capsule mixture. Here, when used at less than 3 wt %, the capsule is too hard so that it is difficult to make the capsule soft, and when used at more than 5 wt %, capsule binding strength is severely decreased, so that the double capsule is not easily broken.

In addition, the coloring agent is used for concealing a charcoal color so that the dark color of charcoal used in the primary capsule is not shown. As the coloring agent, titanium dioxide having both hiding power and polishing power is most preferred, and due to the hiding power of silica also, when silica or a mixture thereof (20 to 40 parts by weight of silica based on 100 parts by weight of titanium dioxide) is used, a white toothpaste composition may be produced. The coloring agent is used at 30-65 wt % with respect to the double capsule mixture. An appearance of the double capsule may be changed to a color other than white by iron oxide, magnesium carbonate, calcium carbonate, manganese violet, zinc oxide, ultramarine blue, a lake pigment, and the like which are raw materials of the coloring agent, thereby manufacturing a capsule which may have various appearance colors. In particular, when titanium dioxide is used as the coloring agent, it may serve as a polishing agent, and thus, a polishing effect of a toothpaste composition may be further improved. Here, when the coloring agent is used at less than 30 wt %, coloring efficiency is lowered, and when used at 65 wt % or more, the content of the primary capsule is relatively decreased and the content of charcoal is also decreased, thereby decreasing the whitening efficacy of a composition.

The double capsule powder is produced by spray-drying the double capsule dispersion to remove the second solvent, which is then subjected to sieve classification to selectively produce powder having an average diameter of 500 μm or less, particularly 150 μm to 300 μm. In addition, preferably, the double capsule may have the average diameter larger than the average diameter of the primary capsule.

Hereinafter, the present invention will be described in more detail by the following Examples. However, the following Examples are only to assist in the understanding of the present invention, and the scope of the present invention is not limited thereto in any sense.

Example 1

In order to produce primary capsule powder, first, 300 g of distilled water and 30 g of corn starch (product name: Corn Starch) as a first binder were dissolved at 110° C. for 1 hour in a 2,000 mL vessel. Then, 67 g of polyglyceryl-10 stearic acid (product name: Almax 9060) as a dispersing agent was dissolved, while supplementing the dispersion with 1,550 g of distilled water. Thereafter, when a temperature of a dispersion reached 50° C. or less, 900 g of coconut charcoal (FIG. 1, product name: SpecKare™ CAC3) was added to the dispersion, and the dispersion was mixed and dispersed to prepare a primary capsule dispersion. The primary capsule dispersion was supplied into a spray drier rotating at a high speed and dried to obtain the primary capsule powder. The obtained primary capsule powder was subjected to sieve classification so that the powder has an outer diameter of 200 μm or less, to screen the primary capsule powder, thereby obtaining primary capsule powder having a black surface as shown in FIG. 2 (particle size: 150 μm, yield=60%).

Meanwhile, in order to produce double capsule powder, 500 g of ethanol, 50 g of ethyl cellulose (product name: EN-N10) as a second binder, and a lauric acid (product name: PALMAC 98-12) as a softening agent were added to a 2000 mL beaker and dissolved. Then, 448 g of titanium dioxide (product name: Purolan E-171-A) and 150 g of silica (product name: AEROSIL® 200) as a coloring agent were added thereto, and the dispersion was mixed and dispersed while being supplemented with 1,000 g of ethanol. Thereafter, 320 g of the primary capsule was input in portions to prepare a double capsule dispersion. The double capsule dispersion was supplied into a spray drier rotating at a high speed and dried to obtain the double capsule powder. The double capsule powder was subjected to sieve classification so that the powder has an outer diameter of 300 μm or less, to screen the double capsule, thereby obtaining double capsule powder having a white surface as shown in FIG. 3 (particle size: 150-300 μm, yield=50%). Compositions of the primary capsule and the double capsule are also shown in Table 1.

Example 2

Uniform particles were selected in the same manner as in Example 1, except that 37 g of corn starch and 60 g of Almax 9060 were used.

Example 3

Uniform particles were selected in the same manner as in Example 1, except that 44 g of corn starch and 53 g of Almax 9060 were used.

Example 4

Uniform particles were selected in the same manner as in Example 1, except that 51 g of corn starch and 46 g of Almax 9060 were used.

Example 5

Uniform particles were selected in the same manner as in Example 1, except that 58 g of corn starch and 39 g of Almax 9060 were used.

Example 6

Uniform particles were selected in the same manner as in Example 1, except that 65 g of corn starch and 32 g of Almax 9060 were used.

Example 7

Uniform particles were selected in the same manner as in Example 1, except that 72 g of corn starch and 25 g of Almax 9060 were used.

Example 8

Uniform particles were selected in the same manner as in Example 1, except that 79 g of corn starch and 18 g of Almax 9060 were used.

Example 9

Uniform particles were selected in the same manner as in Example 1, except that 86 g of corn starch and 11 g of Almax 9060 were used.

Example 10

Uniform particles were selected in the same manner as in Example 1, except that 93 g of corn starch and 4 g of Almax 9060 were used.

Example 12

Uniform particles were selected in the same manner as in Example 1, except that 47 g of EC-N10 and 33 g of PALMAC 98-12 were used.

Example 13

Uniform particles were selected in the same manner as in Example 1, except that 44 g of EC-N10 and 36 g of PALMAC 98-12 were used.

Example 14

Uniform particles were selected in the same manner as in Example 1, except that 41 g of EC-N10 and 39 g of PALMAC 98-12 were used.

Example 15

Uniform particles were selected in the same manner as in Example 1, except that 38 g of EC-N10 and 42 g of PALMAC 98-12 were used.

Example 16

Uniform particles were selected in the same manner as in Example 1, except that 35 g of EC-N10 and 45 g of PALMAC 98-12 were used.

Example 17

Uniform particles were selected in the same manner as in Example 1, except that 32 g of EC-N10 and 48 g of PALMAC 98-12 were used.

Example 18

Uniform particles were selected in the same manner as in Example 1, except that 29 g of EC-N10 and 343 g of the primary capsule were used.

Example 19

Uniform particles were selected in the same manner as in Example 1, except that 26 g of EC-N10 and 361 g of the primary capsule were used.

Example 20

Uniform particles were selected in the same manner as in Example 1, except that 23 g of EC-N10 and 376 g of the primary capsule were used.

TABLE 1

| | | First binder | Dispersing agent | Charcoal powder | |
|---|---|---|---|---|---|
| Composition ratio of primary capsule | Example 1 | 3.0 | 6.7 | 90.3 | |
| | Example 2 | 3.7 | 6.0 | 90.3 | |
| | Example 3 | 4.4 | 5.3 | 90.3 | |
| | Example 4 | 5.1 | 4.6 | 90.3 | |
| | Example 5 | 5.8 | 3.9 | 90.3 | |
| | Example 6 | 6.5 | 3.2 | 90.3 | |
| | Example 7 | 7.2 | 2.5 | 90.3 | |
| | Example 8 | 7.9 | 1.8 | 90.3 | |
| | Example 9 | 8.6 | 1.1 | 90.3 | |
| | Example 10 | 9.3 | 0.4 | 90.3 | |
| | | Second binder | Softening agent | Coloring agent | Primary capsule |
| Composition ratio of double capsule | Example 11 | 5.0 | 3.0 | 59.8 | 32.2 |
| | Example 12 | 4.7 | 3.3 | 59.8 | 32.2 |
| | Example 13 | 4.4 | 3.6 | 59.8 | 32.2 |
| | Example 14 | 4.1 | 3.9 | 59.8 | 32.2 |
| | Example 15 | 3.8 | 4.2 | 59.8 | 32.2 |
| | Example 16 | 3.5 | 4.5 | 59.8 | 32.2 |
| | Example 17 | 3.2 | 4.8 | 59.8 | 32.2 |
| | Example 18 | 2.9 | 3.0 | 59.8 | 34.3 |
| | Example 19 | 2.6 | 3.0 | 59.8 | 34.6 |
| | Example 20 | 2.3 | 3.0 | 59.8 | 34.9 |

Experimental Example 1: Measurement of Particle Breakability

The capsule particle breakability was measured by applying a constant load of 5 gf/cm² to the primary capsule powder prepared in Examples 1 to 10 and 0.3 g of the double capsule manufactured in Examples 11 to 20, while performing a repeated vertical and horizontal movement at a constant speed of 0.01 m/sec for 30 seconds. This was observed by an optical microscope, the number of broken particles per a 1 mm×1 mm pixel was counted three times, an average value thereof was calculated, and primary capsule breakability is shown in Table 2 and double capsule breakability is shown in Table 3. Further, a photograph of a broken double capsule is shown in FIG. 4. Here, the less the number of normal particles is, the better the breakability is.

TABLE 2

| Primary capsule | Examples | | | | | | | | | |
|---|---|---|---|---|---|---|---|---|---|---|
| | 1 | 2 | 3 | 4 | 5 | 6 | 7 | 8 | 9 | 10 |
| Capsule particle breakability (number of normal particles) | 4-6 | 6-8 | 8-10 | 10-12 | 12-14 | 14-16 | 0-2 | 1-3 | 16-18 | 18-20 |

As shown in Table 2, breakability was measured by adjusting the contents of the binder and the dispersing agent. The content of the binder is the most important variable and an overall trend in which the more the content is, the higher the capsule strength is, may be seen, but as confirmed in the experiments of Examples 7 and 8, it was found that when the binder and the dispersing agent form an appropriate ratio, breakage of the primary capsule becomes easy.

TABLE 3

| Double capsule | Examples | | | | | | | | | |
|---|---|---|---|---|---|---|---|---|---|---|
| | 11 | 12 | 13 | 14 | 15 | 16 | 17 | 18 | 19 | 20 |
| Capsule particle breakability (number of normal particles) | 23~21 | 21~18 | 18~15 | 15~13 | 13~11 | 11~9 | 9~7 | 7~5 | 5~3 | 3~0 |

As shown in FIG. 4, it was confirmed that the double capsule powder had a black color by the breakage. As shown in Table 3, it was found that as the content of the second binder is decreased, the breakability is increased, and the number of normal capsules is gradually decreased. When the number of normal capsules is large and the breakability is not good, in the case of a toothpaste composition in which a core material, charcoal is present, the charcoal component may not efficiently serve as a whitening agent inside the mouth. Thus, selection of an appropriate content of the raw material should be noted when selecting a capsule composition, and a capsule which is not broken within a certain period of time may give a feeling of use similar to that of a foreign matter, and thus, attention should be paid during manufacture.

Experimental Example 2: Sensory Evaluation of Toothpaste Composition

Comparative Example 1

In order to identify an influence on the strength of the primary capsule or the double capsule in the charcoal-containing toothpaste composition, only the primary capsule of Example 7 having low capsule strength was used. Each of 15 g of (sodium hydrogen carbonate), 20 g of (glycerin), 15 g of (gelatin), and 150 g of (essence oil) which are the materials of the toothpaste composition was mixed with 300 g of the primary capsule to manufacture a toothpaste composition. Each composition is also shown in Table 4.

For sensory evaluation, 1 g of the toothpaste composition was spread on a flat test board so that the same pressure was applied, a toothbrush was attached to a weight of 50 g having a size of 20×20×10 mm, a repeated movement was performed identically 10 times, and then a capsule state was confirmed. Only the portion where the toothbrush adjoined the composition and friction strength was directly received was visually observed, and the capsule state included in the composition was confirmed and is shown in Table 5.

Comparative Example 2

A toothpaste composition was manufactured in the same manner as in Comparative Example 1, except that the primary capsule of Example 10 having high capsule strength was used instead of using the primary capsule of Example 7.

Comparative Example 3

A toothpaste composition was manufactured in the same manner as in Comparative Example 1, except that the primary capsule of Example 3 having high capsule strength was used instead of using the primary capsule of Example 7.

Example 21

A toothpaste composition was manufactured in the same manner as in Comparative Example 1, except that the double capsule of Example 7 having low breakability was used instead of using the primary capsule of Example 7.

Example 22

A toothpaste composition was manufactured in the same manner as in Comparative Example 1, except that the double capsule of Example 10 having high breakability was used instead of using the primary capsule of Example 7.

Example 23

A toothpaste composition was manufactured in the same manner as in Comparative Example 1, except that the double capsule of Example 3 having moderate breakability was used instead of using the primary capsule of Example 7.

TABLE 4

| Raw material name | Comparative Example 1 | Comparative Example 2 | Comparative Example 3 | Example 21 | Example 22 | Example 23 |
|---|---|---|---|---|---|---|
| Sodium hydrogen carbonate (g) | | | 15 | | | |
| Glycerin (g) | | | 20 | | | |
| Gelatin (g) | | | 15 | | | |
| Essence oil (g) | | | 150 | | | |
| Primary capsule (g) | | 300 | | | — | |
| Double capsule (g) | | — | | | 300 | |

TABLE 5

| | Sensory evaluation | | Sensory evaluation |
|---|---|---|---|
| Comparative Example 1 | o | Example 21 | o |
| Comparative Example 2 | x | Example 22 | x |
| Comparative Example 3 | x | Example 23 | x |

(when the adjoining portion turned black: o, when the adjoining portion partially turned black: x)

From the results of Table 5, it was found that when the primary capsule strength was high, the stability and the strength of the double capsule were also influenced, and thus, the capsule was not easily broken when applying the capsule to the composition. Only when the content and the kind of binder which is a core material of strength and the ratio of the dispersing agent which has an influence thereon were appropriately used, the double capsule which may be used in the toothpaste composition may be manufactured.

Experimental Example 3: Confirmation of Breakability of Toothpaste Composition by Tooth Brushing Example 24

Example 10 (low breakability, binder content of 23 g) and Example 1 (high breakability, binder content of 50 g) were selected from the compositions manufactured in the capsule composition ratios to manufacture a toothpaste composition. 15 g of a polishing agent (product name: sodium hydrogen carbonate), 20 g of a moisturizer (product name: glycerin), 15 g of a stabilizer (product name: gelatin), 150 g of an antimicrobial agent (product name: essence oil), and a charcoal-containing double capsule (300 g) which are used in the toothpaste manufacture, respectively were mixed to manufacture a toothpaste composition. Randomly selected 10 children, 10 adults, and 10 seniors were classified into three age to occupation groups and brushed their teeth the same number of times (three times) using the thus-manufactured toothpaste composition, and then the breakability was confirmed and is shown in Table 6. When each of three people at the ages of 8, 23, and 70 used a similar amount and it was visually confirmed that most of the toothpaste composition remaining in the tooth in a brushed area turned black, the capsule was identified as broken.

Example 25

The experimental subject was selected in the same manner as in Example 11, except that the subject group was randomly selected from those at the ages of 7, 16, and 68 without departing from the range group.

Example 26

The experimental subject was selected in the same manner as in Example 11, except that the subject group was randomly selected from those at the ages of 8, 17, and 67 without departing from the range group.

Example 27

The experimental subject was selected in the same manner as in Example 11, except that the subject group was randomly selected from those at the ages of 8, 20, and 65 without departing from the range group.

Example 28

The experimental subject was selected in the same manner as in Example 11, except that the subject group was randomly selected from those at the ages of 7, 20, and 66 without departing from the range group.

Example 29

The experimental subject was selected in the same manner as in Example 11, except that the subject group was randomly selected from those at the ages of 8, 19, and 66 without departing from the range group.

Example 30

The experimental subject was selected in the same manner as in Example 11, except that the subject group was randomly selected from those at the ages of 9, 28, and 67 without departing from the range group.

Example 31

The experimental subject was selected in the same manner as in Example 11, except that the subject group was randomly selected from those at the ages of 9, 29, and 68 without departing from the range group.

Example 32

The experimental subject was selected in the same manner as in Example 11, except that the subject group was randomly selected from those at the ages of 8, 28, and 67 without departing from the range group.

Example 33

The experimental subject was selected in the same manner as in Example 11, except that the subject group was randomly selected from those at the ages of 10, 31, and 67 without departing from the range group.

TABLE 6

| Capsule strength | At the age of 6-12 (children) | | At the age of 13-44 (youth and adult) | | At the age of 65- (senior) | |
|---|---|---|---|---|---|---|
| | Low | High | Low | High | Low | High |
| Example 24 | ○ | ○ | ○ | ○ | x | x |
| Example 25 | ○ | x | ○ | ○ | ○ | x |
| Example 26 | ○ | x | ○ | ○ | ○ | ○ |
| Example 27 | x | x | ○ | ○ | ○ | x |
| Example 28 | ○ | x | ○ | ○ | x | x |
| Example 29 | ○ | x | ○ | x | ○ | x |
| Example 30 | ○ | ○ | ○ | ○ | ○ | x |
| Example 31 | ○ | x | ○ | ○ | x | ○ |
| Example 32 | ○ | x | ○ | ○ | ○ | x |
| Example 33 | ○ | ○ | ○ | ○ | x | x |

(○: the toothpaste composition turned black, x: the toothpaste composition changed only partially or did not turn black)

As shown in Table 6, the capsule manufactured by adjusting the content of the binder was used to confirm the capsule breakability by an age group. After the capsule was manufactured with the capsule strength being classified into high/low depending on the composition content, a degree to which the capsule was broken and a black color which is an original charcoal color came out to the teeth was confirmed by each occupation. It was found that in the youth and adult groups having relatively high muscular strength, the capsule was all easily broken even in the case in which the capsule strength was high, but in the child and senior groups, the toothpaste composition did not entirely turn black when a strong capsule was manufactured. When the raw material used in the capsule was appropriately adjusted to adjust strength, the capsule may be selectively manufactured at the time of being applied to the toothpaste composition.

Experimental Example 4: Stability Confirmation of Toothpaste Composition

Example 34

In order to test the stability of the toothpaste physical properties, original physical properties should not be deteriorated after storing the toothpaste at room temperature for 30 months after manufacture, and also, should not be deteriorated even after storing the toothpaste for 3 months at 50° C. which is a similar condition to the state after 30 months have passed since production. The double capsule toothpaste composition of Example 23 was stored for 2 weeks under a harsh condition of 70° C./50% using a thermo-hygrostat, and then a whitening test was performed. As an experimental condition, 10 people having a relatively dark tooth color of an A3 grade or lower were selected and how the whitening effect was changed when they brushed their teeth three times a day for a week, was selected. Then, each of the toothpaste compositions stored in the thermo-hygrostat was taken out every two weeks, each experimental subject brushed teeth similar times of three times a day, and grade change for the tooth color was observed using the tooth comparison chart classified into 16 steps. The experimental results are shown in Table 7.

Example 35

The whitening test was performed after storage for 4 weeks under the same thermo-hygrostat conditions.

Example 36

The whitening test was performed after storage for 6 weeks under the same thermo-hygrostat conditions.

Example 37

The whitening test was performed after storage for 8 weeks under the same thermo-hygrostat conditions.

Example 38

The whitening test was performed after storage for 10 weeks under the same thermo-hygrostat conditions.

Example 39

The whitening test was performed after storage for 12 weeks under the same thermo-hygrostat conditions.

Example 40

The whitening test was performed after storage for 14 weeks under the same thermo-hygrostat conditions.

Example 41

The whitening test was performed after storage for 16 weeks under the same thermo-hygrostat conditions.

Example 42

The whitening test was performed after storage for 18 weeks under the same thermo-hygrostat conditions.

Example 43

The whitening test was performed after storage for 20 weeks under the same thermo-hygrostat conditions.

TABLE 7

| | | Charcoal double capsule toothpaste composition | | |
|---|---|---|---|---|
| | | Tooth grade (before) | Tooth grade (after) | Grade change |
| Example 34 | Week 2 | D3 | D3 | +2 |
| Example 35 | Week 4 | A3.5 | B3 | +1 |
| Example 36 | Week 6 | D3 | D4 | +2 |
| Example 37 | Week 8 | A3 | D4 | +1 |
| Example 38 | Week 10 | B4 | B3 | +2 |
| Example 39 | Week 12 | B4 | B4 | 0 |
| Example 40 | Week 14 | A3.5 | D3 | +0 |
| Example 41 | Week 16 | B3 | D3 | +1 |
| Example 42 | Week 18 | B3 | D3 | +2 |
| Example 43 | Week 20 | B4 | A3.5 | +1 |

As shown in Table 7, it was found that usually at room temperature and even under the harsh constant temperature and constant humidity conditions, the whitening function was similar to the initial function even after 20 weeks or more.

Experimental Example 5: Confirmation of Double Capsule Efficacy in Cleansing Foam Composition Comparative Example 4

In order to identify the influence on pores when the charcoal-containing double capsule was applied to a foam cleanser, 80 g of purified water, 75 g of a surfactant (product name: Apple Wash), 2 g of an antioxidant (product name: green tea extract), 1 g of a natural preservative (product name: Nafrey), and 2 g of a skin moisturizer (product name: d-panthenol powder) were mixed to manufacture a foam cleansing composition (see Table 8). Thereafter, in order to obtain objective data for a pore condition, a skin diagnosis system (manufacturer: Bomtech, product name: SDM) was used to measure a pore condition, three people (at the age of 23) were selected from a woman group aged 20 to 35 who were not in a good pore condition (randomly selected from people who did not have good pore results in a radial graph as a result of SDM equipment measurement), these people washed their face morning and evening twice a day for 2 weeks using the foam cleanser, and measurement was performed again to observe their pore condition, which is shown in Table 9.

Comparative Example 5

A foam cleansing composition was manufactured in the same manner as in Comparative Example 4, and the implementation and the measurement were performed in the same manner except that one woman aged 20 to 35 (at the age of 32) who was not in a good pore condition was randomly selected.

Example 44

A foam cleansing composition was manufactured in the same manner as in Comparative Example 4, except that 80 g of the charcoal-containing double capsule and 110 g of purified water were used. The implementation and the measurement were performed in the same manner except that one woman aged 20 to 35 (at the age of 28) who was not in a good pore condition was randomly selected.

Example 45

A foam cleansing composition was manufactured in the same manner as in Comparative Example 4, except that 80 g of the charcoal-containing double capsule and 110 g of purified water were used. The implementation and the measurement were performed in the same manner except that one woman aged 20 to 35 (at the age of 30) who was not in a good pore state was randomly selected.

Example 46

A foam cleansing composition was manufactured in the same manner as in Comparative Example 4, except that 80 g of the charcoal-containing double capsule and 110 g of purified water were used. The implementation and the measurement were performed in the same manner except that one woman aged 25 to 39 (at the age of 35) who was in a bad pore condition was randomly selected.

TABLE 8

|   |   | Comparative Example 4 | Comparative Example 5 | Example 44 | Example 45 | Example 46 |
|---|---|---|---|---|---|---|
| 1 | d-Panthenol |  |  | 2 g |  |  |
| 2 | Apple Wash |  |  | 75 g |  |  |
| 3 | Green tea extract |  |  | 2 g |  |  |
| 4 | Nafrey |  |  | 1 g |  |  |
| 5 | Purified water | 80 g |  |  | 110 g |  |
| 6 | Double capsule | — |  |  | 80 g |  |

TABLE 9

|   | Before experiment | After experiment |
|---|---|---|
| Comparative Example 4 | Step 3 | Step 3 |
| Comparative Example 5 | Step 3 | Step 2 |
| Example 44 | Step 3 | Step 2 |
| Example 45 | Step 3 | Step 2 |
| Example 46 | Step 3 | Step 1 |

As a result of SDM measurement, a total of 6 items of data for oil, moisture, elasticity, wrinkles, pigmentation, and pores was derived as a radial graph, and in the present experiment, only an item measurement value for digitization of pores was referenced. The radial graph represents degrees as a total of three different sized circle shapes, which may be classified into each of the outermost circle for step 1 (skin care for maintaining the present state and prevention is needed), the middle circle for step 2 (continuous skin care is needed), and the middle circle for step 3 (intensive skin care for improvement is needed). As the experimental occupation, people corresponding to step 3 within the age category were selected.

As shown in Table 9, in the absence of the charcoal-containing double capsule, when pores were observed after using the foam cleanser, no improvement or not great change was confirmed. However, in the results of Examples 44 to 46, the pore condition was all improved, and, in particular, in Example 46, it was confirmed that the pore condition was greatly improved in two weeks.

In the above experiment, other result values for the skin condition were not considered, and the result values were derived by measuring only the pore condition without separate consideration of the variables for dead skin cell conditions, skin type, makeup cosmetics used, and toner use of each test subject.

Experimental Example 6: Evaluation in Cleaning Foam Composition Containing Double Capsule Example 47

In order to evaluate a feeling of use of the cleansing foam manufactured in Example 44, 10 women usually having no side effect when they washed their face using a foam cleanser were selected from women aged 20 to 35, and the items according to the following Table 7 were evaluated according to each criterion, according to the most common way of washing faces. Comparative Example 6 targeted a commercial product in which charcoal powder prepared by a preparation method different from the present invention was simply mixed. The scores for evaluation items were 5 for very good, 4 for good, 3 for average, 2 for unsatisfactory, and 1 for poor, and when the determination criterion was not clear for each item, a decimal point was applied. The final results as an average value of 10 people are shown in Table 10.

TABLE 10

| Experimental item | Comparative Example 4 | Example 2 |
|---|---|---|
| Composition image | 2.9 | 4.7 |
| Rolling sensitivity | 3.4 | 4.4 |
| Washability | 4.5 | 4.3 |
| Skin feeling after washing | 4.6 | 4.5 |

As shown in Table 10, washability and skin feeling after washing were almost similar or did not have a large difference as compared with the conventional product, while the conventional product did not have a good image immediately before use due to the dark color of the composition itself. The rolling sensitivity was evaluated better in the charcoal-containing double capsule composition than the conventional simple charcoal-mixed product. It was intended to obtain data results of minimized subjectivity by performing each test without mentioning that charcoal was used as a raw material component, in order not to give preconception for the component during the test for experiment items.

As described above, although the present invention has been described with reference to limited exemplary embodiments and drawings, it would be appreciated by those skilled in the art that the present invention is not limited thereto but various modifications and alterations might be made without departing from the scope defined in the range of equivalents of the following claims.

The invention claimed is:

1. A charcoal-containing double capsule comprising consisting of:
   a softening agent, a second binder, a coloring agent, and a primary capsule containing a dispersing agent, charcoal powder, and a first binder, wherein the charcoal powder is bound to the first binder,
   wherein the primary capsule and the coloring agent are bound to the second binder,
   wherein the first binder is a modified starch selected from the group consisting of acetylated distarch adipate, acetylated distarch phosphate, starch sodium octenyl succinate, distarch phosphate, monostarch phosphate, phosphated distarch phosphate, starch acetate, and hydroxypropyl distarch phosphate; or a natural starch selected from the group consisting of a wheat starch, a rice starch, a potato starch, and a corn starch,
   wherein the dispersing agent is any one selected from the group consisting of polyglyceryl-2 oleyl ether, polyglyceryl-6 pentaoleate, polyoxyethylene glyceryl monostearate, and polyglyceryl-10 stearate,
   wherein the softening agent is any one selected from the group consisting of a lauric acid and a palmitic acid,
   wherein the coloring agent is a mixture of titanium dioxide and silica, and
   wherein the primary capsule contains 70-94 wt % of the charcoal powder, with respect to 100 wt % of the primary capsule.

2. The charcoal-containing double capsule of claim 1, wherein the primary capsule has an average diameter of 10 μm to 200 μm and the double capsule has an average diameter of 150 μm to 300 μm.

3. The charcoal-containing double capsule of claim 1, wherein charcoal is any one or two or more of activated charcoal forms of a bamboo charcoal, an oak charcoal, and a coconut charcoal.

4. The charcoal-containing double capsule of claim 1, wherein the second binder is one or two or more selected from natural substance-derived polymers selected from the group consisting of ethyl cellulose, methyl cellulose, hydroxylpropyl cellulose, casein, and shellac; ammonium methacrylate-based polymers, methacrylic acid-based polymers, 2-dimethylaminoethyl methacrylate-based polymers, chlorotrimethylammoniumethyl methacrylate-based polymers, and copolymers thereof.

5. A method for manufacturing the charcoal-containing double capsule of claim 1, the method comprising:
   1) Dissolving a first binder in a first solvent to produce a solution in which the first binder is dissolved;
   2) Dissolving a dispersing agent in the solution obtained in 1);
   3) Adding charcoal powder to the solution obtained in 2) and performing homogenous mixing to produce a dispersion in which the charcoal powder is bound to the first binder;
   4) spray-drying the dispersion obtained in 3) to produce a primary capsule powder from which the first solvent is removed;
   5) dissolving a second binder and a softening agent in a second solvent to produce a solution in which the second binder and the softening agent are dissolved;
   6) homogeneously mixing a coloring agent and a dispersing agent with the solution obtained in 5);
   7) mixing the primary capsule powder with the solution obtained in 6) to produce a double capsule dispersion in which the primary capsule is bound to the second binder; and
   8) Spray-drying the double capsule dispersion to produce a double capsule powder from which the second solvent is removed,
   wherein the first binder is a modified starch selected from the group consisting of acetylated distarch adipate, acetylated distarch phosphate, starch sodium octenyl succinate, distarch phosphate, monostarch phosphate, phosphated distarch phosphate, starch acetate, and hydroxypropyl distarch phosphate; or a natural starch selected from the group consisting of a wheat starch, a rice starch, a potato starch, and a corn starch,
   wherein the dispersing agent is any one selected from the group consisting of polyglyceryl-2 oleyl ether, polyglyceryl-6 pentaoleate, polyoxyethylene glyceryl monostearate, and polyglyceryl-10 stearate,
   wherein the softening agent is any one selected from the group consisting of a lauric acid and a palmitic acid,
   wherein the coloring agent is a mixture of titanium dioxide and silica, and
   wherein the primary capsule contains 70-94 wt % of the charcoal powder, with respect to 100 wt % of the primary capsule.

6. The method for manufacturing the charcoal-containing double capsule of claim 5, wherein the first solvent is distilled water.

7. The method for manufacturing the charcoal-containing double capsule of claim 5, wherein the charcoal powder is any one of a bamboo charcoal, an oak charcoal, and a coconut charcoal.

8. The method for manufacturing the charcoal-containing double capsule of claim 5, wherein the second solvent is any one or two or more selected from the group consisting of ethanol, glycerin, 1,2-propanediol, 1,3-propanediol, 1,3-butanediol, 1,4-butanediol, 1,6-hexanediol, and 1,8-octanediol.

9. The method for manufacturing the charcoal-containing double capsule of claim 5, wherein the second binder is any one or two or more selected from natural substance-derived polymers selected from the group consisting of ethyl cellulose, methyl cellulose, hydroxylpropyl cellulose, casein, and shellac; ammonium methacrylate-based polymers, methacrylic acid-based polymers, 2-dimethylaminoethyl methacrylate-based polymers, chlorotrimethylammoniumethyl methacrylate-based polymers, and copolymers thereof.

10. The method for manufacturing the charcoal-containing double capsule of claim 5, wherein the primary capsule has an average diameter of 10 μm to 200 μm and the double capsule has an average diameter of 150 μm to 300 μm.

11. The charcoal-containing double capsule of claim 1, wherein the double capsule is used as an active ingredient of toothpaste.

12. The charcoal-containing double capsule of claim 1, wherein the double capsule is used as an active ingredient of cosmetic formulation.

\* \* \* \* \*